United States Patent
Massot

(10) Patent No.: US 8,322,337 B2
(45) Date of Patent: Dec. 4, 2012

(54) FLUID PRODUCT DISPENSING DEVICE

(75) Inventor: Ronan Massot, Vertout (FR)

(73) Assignee: Aptar France SAS, Le Neubourg (FR)

(*) Notice: Subject to any disclaimer, the term of this patent is extended or adjusted under 35 U.S.C. 154(b) by 422 days.

(21) Appl. No.: 12/667,365

(22) PCT Filed: Jul. 1, 2008

(86) PCT No.: PCT/FR2008/051219
§ 371 (c)(1),
(2), (4) Date: Dec. 30, 2009

(87) PCT Pub. No.: WO2009/007638
PCT Pub. Date: Jan. 15, 2009

(65) Prior Publication Data
US 2010/0175697 A1    Jul. 15, 2010

(30) Foreign Application Priority Data

Jul. 3, 2007 (FR) .................................. 07 56240

(51) Int. Cl.
*A61M 16/00* (2006.01)
(52) U.S. Cl. ................................. 128/203.15
(58) Field of Classification Search ........... 128/203.12–203.17, 203.21, 200.14, 128/200.21, 200.23
See application file for complete search history.

(56) References Cited

U.S. PATENT DOCUMENTS

| 7,950,389 B2 * | 5/2011 | Eason et al. | 128/203.12 |
| 2005/0103337 A1 * | 5/2005 | Hickey et al. | 128/203.15 |

FOREIGN PATENT DOCUMENTS

| WO | 03/035509 A1 | 5/2003 |
| WO | 2006/079751 A1 | 8/2006 |
| WO | 2007/096111 A2 | 8/2007 |
| WO | 2008/012458 A2 | 1/2008 |

* cited by examiner

Primary Examiner — Christopher D Koharski
(74) Attorney, Agent, or Firm — Sughrue Mion, PLLC

(57) ABSTRACT

A fluid dispenser device comprising a body (10), said device further including: an elongate flexible strip (20) supporting a plurality of reservoirs (21) each containing a dose of fluid or powder; reservoir-opening means (30) for opening a respective reservoir on each actuation; first displacement means (40) for causing said flexible strip (20) to advance before and/or during and/or after each actuation, so as to bring a full reservoir into register with said reservoir-opening means; and second displacement means (45) for displacing a full reservoir (21) against said opening means (30) each time the device is actuated, the leading end (25) of said flexible strip (20), in the advance direction of said strip, being fastened to a receiver element (50) that is rotatably mounted relative to said body (10), said receiver element (50) being adapted to exert a traction force on said elongate strip (20), said traction force being independent of said first displacement means (40), said traction force being applied on said strip when said second displacement means (45) move the empty reservoir (21) away from said opening means (30) after each actuation.

14 Claims, 3 Drawing Sheets

FLUID PRODUCT DISPENSING DEVICE

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers provided with blister strips is associated with the movement of the strip, and with storage of the used portion of the strip. Thus, depending on the length of the strip, a large space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the diameter of the rolled-up used strip increases progressively.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler provided with a blister strip, in which inhaler, storage of the used strip portion is optimized, and the risk of the strip blocking is minimized.

The present invention thus provides a fluid dispenser device comprising a body, said device further including: an elongate flexible strip supporting a plurality of reservoirs each containing a dose of fluid or powder; reservoir-opening means for opening a respective reservoir on each actuation; first displacement means for causing said flexible strip to advance before and/or during and/or after each actuation, so as to bring a full reservoir into register with said reservoir-opening means; and second displacement means for displacing a full reservoir against said opening means each time the device is actuated; the leading end of said flexible strip, in the advance direction of said strip, being fastened to a receiver element that is rotatably mounted relative to said body, said receiver element being adapted to exert a traction force on said elongate strip, said traction force being independent of said first displacement means, said traction force being applied on said strip when said second displacement means move the empty reservoir away from said opening means after each actuation.

Advantageously, said rotary receiver element is secured to said second displacement means and includes a set of teeth that co-operates with an actuator member that is secured to said body.

Advantageously, said set of teeth co-operates with an anti-return device, such as a finger, so as to prevent said rotary receiver element from turning in the direction opposite to that which is imparted thereto by said actuator member.

Advantageously, said actuator member is approximately triangular in shape, with a point that co-operates with the set of teeth, said point being connected to the body via a first flexible branch and via a second flexible branch.

Advantageously, said first and second branches have different elasticities.

Advantageously, said first branch curves towards the inside of the triangular actuator member.

Advantageously, said second branch curves towards the outside of the triangular actuator member.

Advantageously, said anti-return device is approximately triangular in shape, with a point that co-operates with the set of teeth, said point being connected to the body via a first flexible branch and via a second flexible branch.

Advantageously, said first and second branches have different elasticities.

Advantageously, said first branch curves towards the inside of the triangular actuator member.

Advantageously, said second branch curves towards the outside of the triangular actuator member.

Advantageously, said rotary receiver element includes a fastener rod that is offset relative to its axis of rotation, said leading end of the elongate flexible strip being fastened to said rod.

Advantageously, said opening means comprise a needle that does not move relative to said body, a reservoir being displaced against said needle each time the device is actuated, said needle penetrating into said reservoir so as to empty it by means of an inhalation flow.

Advantageously, said opening means are controlled by the user inhaling, such that the reservoir is opened and emptied simultaneously by said inhalation flow.

These characteristics and advantages and others of the present invention appear more clearly from the following detailed description, given by way of non-limiting example, and with reference to the accompanying drawings, and in which.

Figure 1:
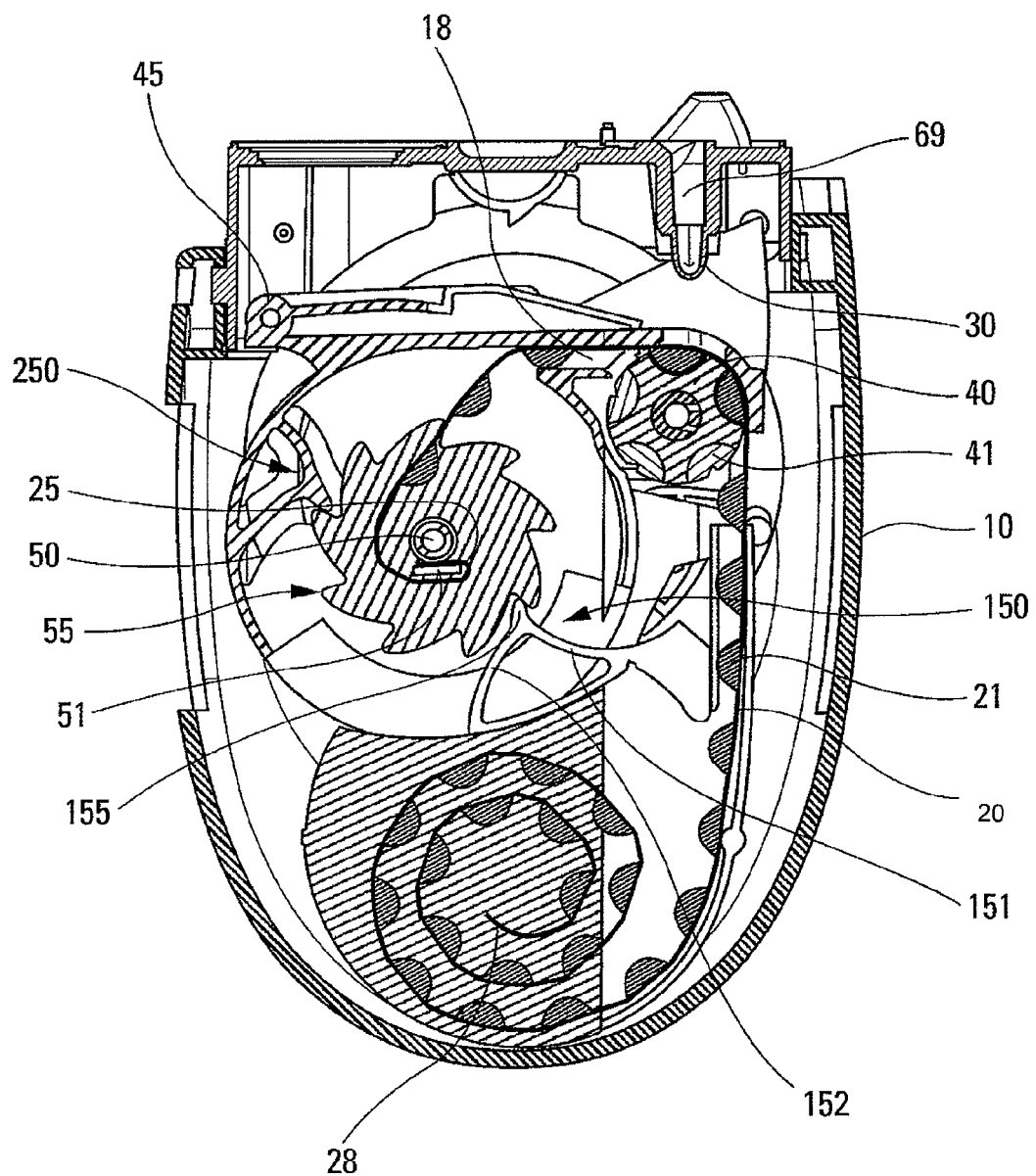
FIG. 1 is a diagrammatic section view showing a dispenser device constituting an advantageous first embodiment of the invention.
Figure 2:
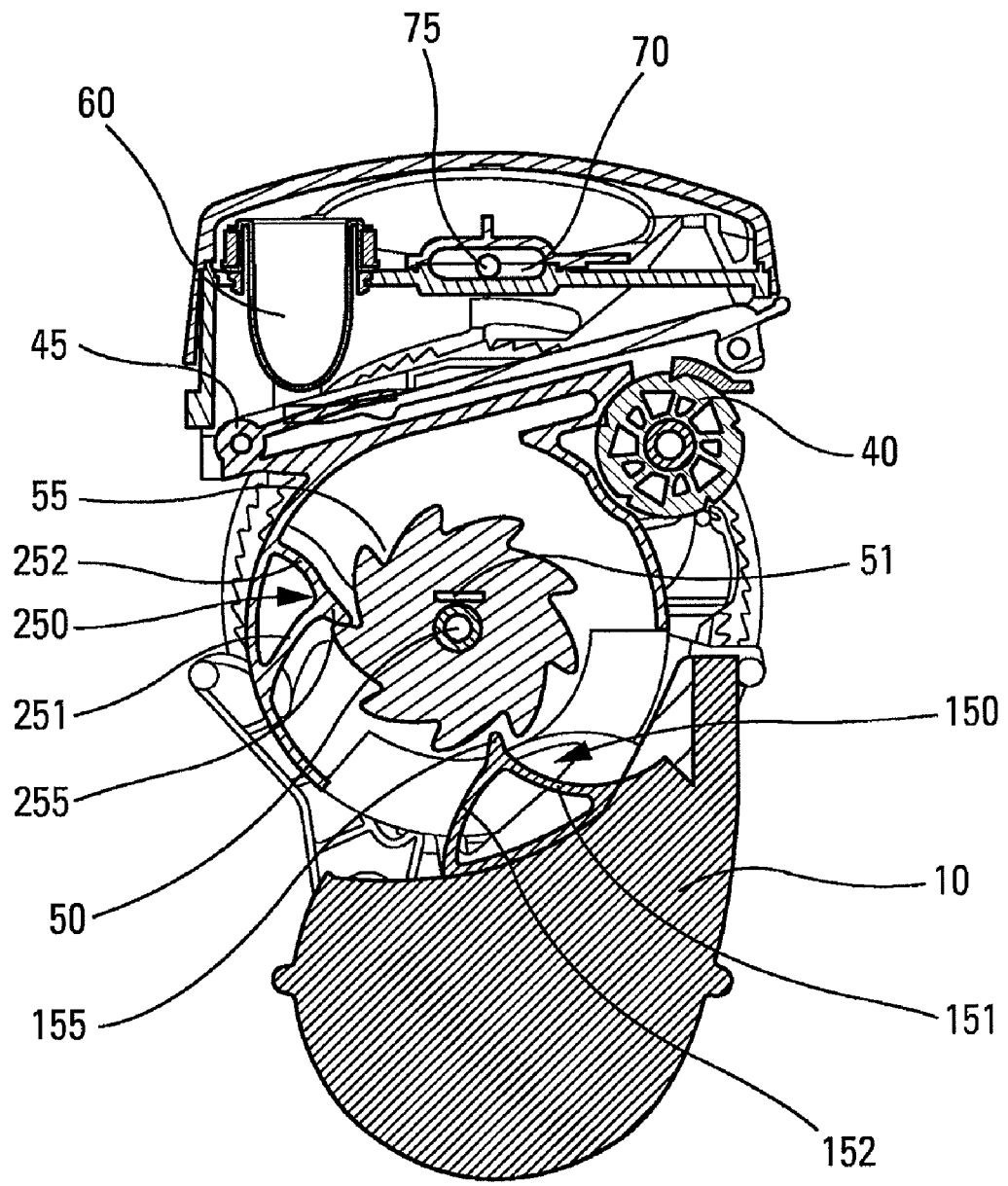
FIG. 2 is a view similar to the view in FIG. 1, showing the device in its actuated position.
Figure 3:
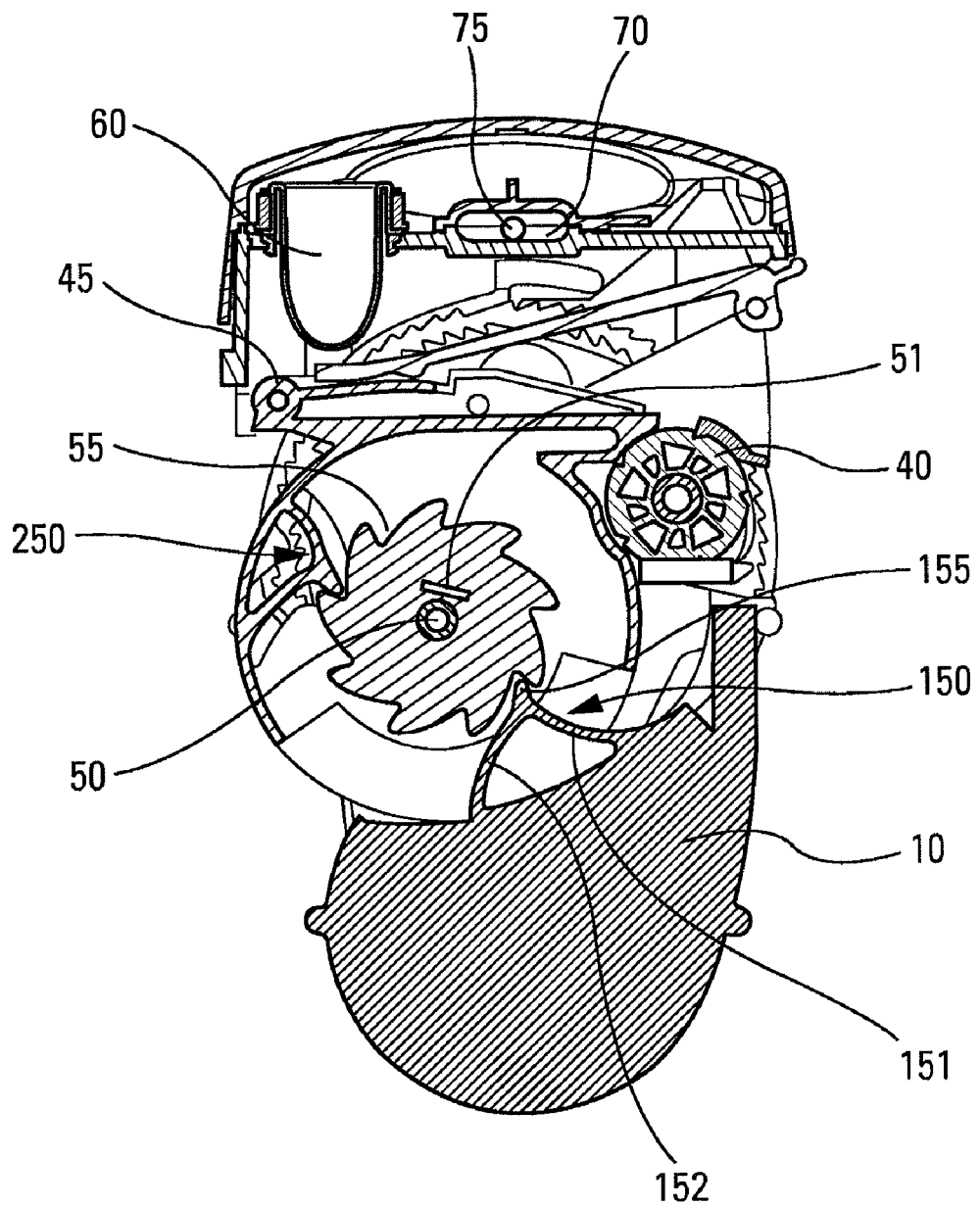
FIG. 3 is a view similar to the view in FIG. 2, after the device has returned to its non-actuated position.

FIGS. 1 to 3 show an advantageous variant embodiment of a dry-powder inhaler. The inhaler includes a body 10 on which there can be slidably mounted two cap-forming portions (not shown) that are adapted to be opened so as to open and load the device. The body 10 can be approximately rounded in shape, as shown in the figures, but it could be of any other appropriate shape. The body 10 includes a mouthpiece or inhaler endpiece (not shown) that defines a dispenser orifice through which the user inhales while the device is being actuated. The caps can be opened by pivoting about a common pivot axis, but any other opening means can be envisaged for opening the device. In a variant, the device could include a single cap instead of two.

Inside the body 10 there is provided a strip 20 of individual reservoirs 21, also known as blisters, said strip being made in the form of an elongate strip 20 on which the blisters 21 are disposed one behind another, in manner known per se. The blisters 21, preferably containing powder, are not shown in FIGS. 2 and 3, so as to avoid cluttering the drawings for the purpose of clarity. The blister strip 20 is advantageously constituted by a base layer or wall that forms the cavities receiving the doses of powder, and by a closure layer or wall that covers each of said blisters 21 in sealed manner. Before first use, the blister strip 20 can be rolled-up inside the body 10, preferably in a storage housing, and first displacement means 40 for displacing the strip are provided for progressively unrolling the blister strip and for causing it to advance. Second displacement means 45 are provided for bringing a respective blister or individual reservoir 21 into a dispensing position each time the device is actuated. The strip portion 25 including the empty reservoirs is advantageously adapted to be rolled-up at another location of said body 10, preferably a reception housing, as described in greater detail below.

The inhaler includes reservoir opening means 30 preferably comprising perforator and/or cutter means for perforating and/or cutting the closure layer of the blisters. For example, the reservoir opening means advantageously comprise a needle 30 that is preferably stationary relative to the body 10, and against which a respective blister 21 is displaced on each actuation by the second displacement means 45. The blister is thus perforated by said needle which penetrates into said blister so as to expel the powder by means of the suction of the user inhaling.

The first displacement means 40 are adapted to cause the blister strip 20 to advance before and/or during and/or after each actuation of the device. The second displacement means 45 are adapted to displace the reservoir 21 to be emptied against said perforator and/or cutter means 30 during actuation. The second displacement means 45 can be urged by a resilient element, such as a spring or any other equivalent resilient element, said resilient element being suitable for being prestressed while the device is being opened. Preferably, the first displacement means 40 comprise an indexer wheel 40 that receives and guides the blisters. Turning the wheel 40 causes the blister strip 20 to advance. In a particular angular position, a given reservoir 21 is always in a position facing the opening means 30. The second displacement means 45 can include a rotary support element that turns about an axis of rotation, said indexer wheel 40 being mounted on said support element.

An actuation cycle of the device can be as follows. While the device is being opened, the two cap-forming lateral portions are moved apart by pivoting on the body in order to open the device and thus load the device. In this position, the indexer wheel 40 cannot be displaced towards the needle 30, since the second displacement means 45 are held by appropriate blocking means. It is while the user is inhaling through the mouthpiece 1 that the blocking means are unblocked, thereby causing said indexer wheel 40 to move towards the needle 30, and thereby causing a reservoir 21 to be opened.

In the embodiments shown, the reservoir 21 is displaced towards its opening position in order to be opened by the needle 30 that is stationary relative to the body 10. However, it is possible to envisage that the needle could also move during the step of opening the reservoir 21. For example, the needle could be displaced towards the reservoir 21 while the reservoir 21 is being displaced towards the needle. In another variant, it is also possible to envisage that the reservoir 21 and the needle are displaced in the same direction during actuation, the reservoir 21 being displaced more quickly in said direction, such that it comes into contact with the needle in order to be opened.

As explained above, it is desirable for the opening means to be actuated by the user inhaling. In order to trigger the reservoir opening means by inhalation, an inhalation trigger system is provided that advantageously comprises a unit 60 that is displaceable and/or deformable under the effect of inhalation, the unit 60 being adapted to release the blocking means.

The unit 60 advantageously comprises a deformable airchamber. Inhalation by the user causes said deformable airchamber to deform, thereby making it possible to release said blocking means and to enable the displacement of the second displacement means 45, and therefore of a respective reservoir 21 towards its opening position. The reservoir 21 is therefore opened only on inhalation, such that it is emptied simultaneously. There is therefore no risk of any dose being lost between the reservoir being opened and the reservoir being emptied.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

The inhaler further includes a dispenser chamber 70 for receiving the dose of powder after a respective reservoir 21 has been opened. The dispenser chamber 70 is advantageously provided with at least one bead 75 that is displaced inside said chamber 70 during inhalation so as to improve dispensing of the air and powder mixture after a reservoir 21 has been opened, in order to increase the effectiveness of the device.

It can be advantageous for the opening means 30, in particular for the needle, to be formed directly on said dispenser chamber 70, e.g. at the end of a channel 69 leading to said chamber 70.

After inhalation, when the user closes the device, all of the components return to their initial, rest position. The device is thus ready for a new utilization cycle.

In an advantageous aspect of the inhaler, the individual reservoirs or blisters 21 are formed on an elongate strip 20 that is initially mainly stored in the form of a roll in a storage housing inside the body 10 of the device. Advantageously, the rolled-up blister strip 20 is held by inner walls of said storage housing without its rear end 28 (rear in the advancement direction of the blister strip 20) being fastened relative to said body 10, thereby enabling the blister-strip roll to be assembled more easily inside the device. The blister strip 20 is displaced by the user, advantageously by means of the indexer wheel 40 that advantageously presents at least one and preferably more recesses 41 having a shape that corresponds to the shape of the blisters. Thus, when the indexer wheel 40 turns, it causes the blister strip 20 to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes.

After opening one or more blisters, the blister-strip portion with the empty reservoirs must be suitable for being stored in easy and compact manner in the device, while avoiding any risk of blockage. Advantageously, the used blister strip is rolled-up automatically, once again forming a roll.

In the invention, the leading end 25 of the blister strip 20 is fastened to a receiver element 50 that is rotatably mounted relative to the body 10. To ensure that the leading portion of the blister strip 20, namely the portion including the empty blisters, is rolled up properly in the reception housing 15, the rotary receiver element 50 is adapted to exert a traction force on the strip 20, in particular on its leading end 25. Thus, any risk is avoided of the strip being rolled up poorly, e.g. folding up concertina-like, etc., which would risk blocking the device.

FIGS. 1 to 3 show an advantageous variant embodiment, in which an actuator member 150 is adapted to co-operate with a set of teeth 55 of the receiver element 50, said actuator member 150 being secured to the body 10. Thus, while said receiver element 50 is being moved relative to the body 10, said actuator member 150 co-operates with the set of teeth 55 so as to turn the receiver element 50.

Preferably, a non-return system 250, such as a finger, also co-operates with the receiver element 50, in particular with the set of teeth 50, so as to prevent the receiver element 50 from turning in the opposite direction to the direction imparted by the actuator member 150.

The traction force exerted by the rotary element 50 on the strip 20 is completely independent of the first displacement means, namely the indexer wheel 40 that causes the strip to advance during each actuation. This makes it possible to guarantee that the traction force does not depend on the diameter of the rolled-up used blister strip, as would occur if the turning of the rotary receiver element 50 was correlated to the turning of the indexer wheel 40.

On the contrary, with the present invention, the receiver element 50 is fastened to a movable portion that moves relative to the body 10 when the second displacement means 45 bring a reservoir 21 against the perforator needle 30. Preferably, the traction force is applied to the blister strip when the second displacement means 45 return to their initial position, after emptying a reservoir. The invention thus makes it possible to apply the same traction force on each actuation.

Advantageously, the leading end 25 of the blister strip 20 is fastened to a fastener rod 51 that is offset relative to the axis of rotation of the receiver element 50. This simplifies assembly and promotes proper rolling up of the strip. It is also possible to envisage other ways of fastening the strip 20 to the receiver element 50, e.g. such as a loop at the leading end 25 of the strip 20, the loop being suitable for being heat-sealed, bonded, or mechanically fastened, or blocking the strip 20 on the receiver element, at the leading end or at a certain distance therefrom, e.g. by means of baffles, or by jamming the strip between the axis and the rod 51 of the receiver element.

Preferably, the actuator member 150 and/or the non-return device 250 can be formed with an approximately triangular shape.

Thus, as shown in the figures, the actuator member 150 can include a point 155 that co-operates with the set of teeth 55 and that is connected to the body 10 via two flexible branches, a first branch 151 and a second branch 152. The non-return device 250 can also include a point 255 and two flexible branches 251 and 252. The elasticity or the flexibility of the first and second branches can be different for the actuator member 150 as for the non-return device 250.

Advantageously, the first branch 151 of the actuator member 150 curves towards the inside of the triangle, and the second branch 152 curves towards the outside of the triangle. Thus, the second branch 152 facilitates bending when the second displacement means 45 brings a reservoir 21 against the needle 30, said bending enabling the point 155 to slide easily over the set of teeth 55 and to become positioned facing the next tooth. While returning in the opposite direction, the first branch 151 enables compression, guaranteeing that the receiver element 50 is properly turned. Naturally, the same can apply for the non-return device 250, as shown in the figures.

Advantageously, the receiver element 50 is disposed approximately at the center of the reception housing. The reception housing can include guide walls, in particular an external guide wall that is curved, e.g. cylindrical, and against which the blister strip 20 slides. An internal guide wall can also be provided at the inlet to the reception housing, and preferably extends approximately parallel to the external guide wall, so as to form a guide channel 18 for the blister strip. The guide walls further facilitate proper rolling up of the blister strip around the receiver element 50.

The present invention therefore makes it possible to provide a dry-powder inhaler that performs the following functions:
 a plurality of individual doses of powder stored in individual sealed reservoirs, e.g. 30 or 60 doses stored on a rolled-up strip;
 the powder is released by perforation that is achieved by the user inhaling, the blister being perforated by means of an inhalation detector system that is coupled to a pre-stressed release system;
 appropriately-shaped drive means that are engaged with blisters so as to displace the blister strip on each actuation, and to bring a new reservoir into a position in which it is to be opened by appropriate opening means; and safe and reliable storage of the used portion of the strip, by being rolled up around a rotary element that is adapted to pull on the strip on each actuation, the traction being completely independent of the first displacement means, namely the indexer wheel 40 that is used to cause the blister strip 20 to advance.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, etc. The prestressing means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A fluid dispenser device comprising:
   a body;
   an elongate flexible strip supporting a plurality of reservoirs each containing a dose of fluid or powder;
   reservoir-opening means for opening a respective reservoir on each actuation;
   first displacement means for causing said flexible strip to advance at least one of before, during and after each actuation, so as to bring a full reservoir into register with said reservoir-opening means; and
   second displacement means for displacing a full reservoir against said opening means each time the device is actuated;
   wherein a leading end of said flexible strip, in the advance direction of said strip, is fastened to a receiver element that is rotatably mounted relative to said body, said receiver element being adapted to exert a traction force on said elongate strip, said traction force being independent of said first displacement means, said traction force being applied on said strip when said second displacement means move the empty reservoir away from said opening means after each actuation;
   said opening means comprises a needle that does not move relative to said body, a reservoir being displaced against said needle each time the device is actuated, said needle penetrating into said reservoir so as to empty the reservoir by an inhalation flow.

2. A device according to claim 1, in which said rotary receiver element is secured to said second displacement means and includes a set of teeth that co-operates with an actuator member that is secured to said body.

3. A device according to claim 2, in which said set of teeth co-operates with an anti-return device, such as a finger, so as to prevent said rotary receiver element from turning in the direction opposite to that which is imparted thereto by said actuator member.

4. A device according to claim 2, in which said actuator member is approximately triangular in shape, with a point that co-operates with the set of teeth, said point being connected to the body via a first flexible branch and via a second flexible branch.

5. A device according to claim 4, in which said first and second branches have different elasticities.

6. A device according to claim 4, in which said first branch curves towards the inside of the triangular actuator member.

7. A device according to claim 4, in which said second branch curves towards the outside of the triangular actuator member.

8. A device according to claim 3, in which said anti-return device is approximately triangular in shape, with a point that co-operates with the set of teeth, said point being connected to the body via a first flexible branch and via a second flexible branch.

9. A device according to claim 8, in which said first and second branches have different elasticities.

10. A device according to claim 8, in which said first branch curves towards the inside of the triangular anti-return device.

11. A device according to claim 8, in which said second branch curves towards the outside of the triangular anti-return device.

12. A device according to claim 1, in which said rotary receiver element includes a fastener rod that is offset relative to its axis of rotation, said leading end of the elongate flexible strip being fastened to said rod.

13. A device according to claim 1, in which said opening means are controlled by the user inhaling, such that the reservoir is opened and emptied simultaneously by said inhalation flow.

14. A fluid dispenser device comprising;
    a body;
    an elongate flexible strip supporting a plurality of reservoirs each containing a dose of fluid or powder;
    a perforator positioned to open a respective reservoir on each actuation;
    an indexer wheel that advances flexible strip at least one of before, during and after each actuation, so as to bring a full reservoir into register with the perforator; and
    a pivoting element that displaces a full reservoir against the perforator each time the device is actuated;
    wherein a leading end of the flexible strip, in an advance direction of the strip, is fastened to a receiver element that is rotatably mounted relative to the body, the receiver element configured to exert a traction force on the elongate strip, wherein the traction force is independent of the indexer wheel, the traction force being applied on the strip when the pivoting element moves the empty reservoir away from the perforator after each actuation;
    wherein the perforator comprises a needle that does not move relative to the body, a reservoir is displaced against the needle each time the device is actuated, and the needle penetrates into the reservoir so as to empty the reservoir by an inhalation flow.

* * * * *